US010081016B2

(12) United States Patent
Cooney et al.

(10) Patent No.: US 10,081,016 B2
(45) Date of Patent: Sep. 25, 2018

(54) MOLECULAR ANALYSIS SYSTEM AND USE THEREOF

(71) Applicant: AKONNI BIOSYSTEMS, INC., Frederick, MD (US)

(72) Inventors: Christopher G. Cooney, Severn, MD (US); Peter Qiang Qu, New Market, MD (US); Arial Bueno, Frederick, MD (US)

(73) Assignee: Akonni Biosystems, Inc., Frederick, MD (US)

( * ) Notice: Subject to any disclaimer, the term of this patent is extended or adjusted under 35 U.S.C. 154(b) by 214 days.

(21) Appl. No.: 14/743,389

(22) Filed: Jun. 18, 2015

(65) Prior Publication Data

US 2015/0367347 A1 Dec. 24, 2015

Related U.S. Application Data

(60) Provisional application No. 62/014,329, filed on Jun. 19, 2014.

(51) Int. Cl.
*B01L 7/00* (2006.01)
*C12M 3/00* (2006.01)

(52) U.S. Cl.
CPC ............ *B01L 7/52* (2013.01); *B01L 2200/12* (2013.01); *B01L 2200/147* (2013.01); *B01L 2300/1822* (2013.01)

(58) Field of Classification Search
CPC .. B01L 7/52; B01L 2200/12; B01L 2200/147; B01L 2300/1822
See application file for complete search history.

(56) References Cited

U.S. PATENT DOCUMENTS

| | | | |
|---|---|---|---|
| 5,741,700 | A | 4/1998 | Ershov et al. |
| 5,770,721 | A | 6/1998 | Ershov et al. |
| 5,981,734 | A | 11/1999 | Mirzabekov et al. |
| 6,656,725 | B2 | 12/2003 | Mirzabekov et al. |
| 8,236,553 | B2 | 8/2012 | Belgrader et al. |
| 8,574,923 | B2 | 11/2013 | Cooney et al. |
| 8,623,789 | B2 | 1/2014 | Belgrader et al. |

(Continued)

FOREIGN PATENT DOCUMENTS

WO 2007064117 6/2007

OTHER PUBLICATIONS

International Search Report issued in PCT Application No. PCT/US2015/036433 dated Sep. 16, 2015.

(Continued)

*Primary Examiner* — Michael L Hobbs
(74) *Attorney, Agent, or Firm* — Michael Ye; Morris, Manning & Martin, LLP

(57) ABSTRACT

A molecular testing device comprises a heating and cooling module having a thin-film thermoelectric heating and cooling device, and a removable test module having a combined amplification and hybridization reaction chamber. The reaction chamber comprises a thermo-conductive exterior surface and a microarray on an interior surface. The thin-film thermoelectric heating and cooling device has a heat transfer surface that is adapted to make contact with the thermo-conductive exterior surface of the reaction chamber. The molecular testing device may be used to perform a PCR in the reaction chamber.

6 Claims, 17 Drawing Sheets

(56) References Cited

U.S. PATENT DOCUMENTS

| | | | |
|---|---|---|---|
| 2003/0175947 | A1 | 9/2003 | Liu et al. |
| 2004/0037739 | A1* | 2/2004 | McNeely .................. B01F 5/10 422/417 |
| 2004/0209331 | A1 | 10/2004 | Ririe |
| 2004/0265884 | A1 | 12/2004 | Knoche |
| 2005/0145273 | A1 | 7/2005 | Atwood et al. |
| 2010/0028205 | A1* | 2/2010 | Ponjee ................ B01L 3/50273 422/68.1 |
| 2012/0196767 | A1 | 8/2012 | Cooney et al. |
| 2014/0073013 | A1 | 3/2014 | Gorman et al. |

OTHER PUBLICATIONS

File History of U.S. Appl. No. 11/425,667, filed Jun. 21, 2006.
D.S. Leland et al., "Role of cell culture for virus detection in the age of technology", Clinical Microbiology Reviews, 20 (1), 2007, 49-78.
Communication pursuant to Rule 164(1) EPC dated Nov. 29, 2017 in European Application No. EP 15 810 073.

* cited by examiner

| AVG SIGNAL | HEATING AND COOLING DEVICE AND REACTION CHAMBER | CONVENTIONAL THERMOCYCLER AND PCR TUBE |
|---|---|---|
| Cy3 | 192289 | 190961 |
| 5 Inf A | 328924 | 821982 |
| 226 STREP | 3853375 | 4562954 |
| 21 STREP | 2123562 | 3522528 |

| SIGNAL/3xstd DEV | | |
|---|---|---|
| Cy3 | 35.7 | 35.7 |
| 5 Inf A | 63.5 | 158.2 |
| 226 STREP | 743.2 | 882.7 |
| 21 STREP | 409.9 | 678.9 |

FIG. 10

MOLECULAR ANALYSIS SYSTEM AND USE THEREOF

This Application claims priority of U.S. Provisional Application No. 62/014,329, filed on Jun. 19, 2014, which is incorporated herein in its entirety by reference.

FIELD

The present application relates generally to molecular analysis systems and, in particular, to molecular analysis systems with thermoelectric heating and cooling devices for detection of biological materials in a sample using the polymerase chain reaction (PCR).

BACKGROUND

Molecular testing is a test carried out at the molecular level for detection of biological materials, such as DNA, RNA and/or proteins, in a test sample. Molecular testing is beginning to emerge as a gold standard due to its speed, sensitivity and specificity. For example, molecular assays were found to be 75% more sensitive than conventional cultures when identifying enteroviruses in cerebrospinal fluid and are now considered the gold standard for this diagnostic (Leland et al., Clin. Microbiol Rev. 2007, 20:49-78).

Molecular assays for clinical use are typically limited to identification of less than six genetic sequences in a single reaction (i.e, real-time PCR assays). Microarrays, which are patterns of molecular probes attached to a solid support, are one way to increase the number of sequences that can be uniquely identified. However, the workflow is typically complex and requires molecular amplification prior to incubation, or hybridization, with the microarray. Separate amplification and hybridization allows the vessels for amplification to be designed for efficient thermal transfer; however, the fluidic complexity is considerable. Combining amplification and hybridization is one way to simplify the fluidics and operational complexity; however, this approach can suffer from thermal transfer inefficiencies because the reaction vessel often consists of a thermally inefficient boundary or support to which the microarrays can be attached.

SUMMARY

One aspect of the present application relates to a molecular testing device. The device comprises a heating and cooling module comprising a thermoelectric heating and cooling device, and a removable test module comprising a combined amplification and hybridization reaction chamber comprising a thermo-conductive exterior surface and a microarray on an interior surface, wherein the thermoelectric device comprises a heat transfer surface that is adapted to make contact with the thermo-conductive exterior surface of said reaction chamber.

Another aspect of the present application relates to a device for performing PCR. The device comprises a heating and cooling module comprising a thermoelectric heating and cooling (TEHC) device comprising a heat transfer surface, a holder for receiving a removable test module comprising a reaction chamber having a thermo-conductive exterior surface, a moving system that brings the heat transfer surface in contact with the thermo-conductive exterior surface when the test module is placed in the holder, and a programmable control module that regulates temperature of the heat transfer surface.

Another aspect of the present application relates to a method for performing PCR on a microarray in a reaction chamber. The method comprises the steps of (a) placing a test module comprising a reaction chamber into a PCR device, wherein the reaction chamber comprises a thermo-conductive exterior surface and a microarray mounted on an interior surface, and wherein the PCR device comprises a heating and cooling module comprising a thermoelectric heating and cooling device with a heat transfer surface and a programmable control module that regulates temperature of the heat transfer surface, (b) bringing the heat transfer surface of the thermoelectric heating and cooling device into contact with the thermo-conductive exterior surface of the reaction chamber; and (c) completing a PCR by heating and cooling the reaction chamber through the heat transfer surface based on a PCR program stored in the control module.

BRIEF DESCRIPTION OF DRAWINGS

FIG. 10 shows exemplary fluorescent signal intensities from microarray spots.

DETAILED DESCRIPTION

Figure 1:
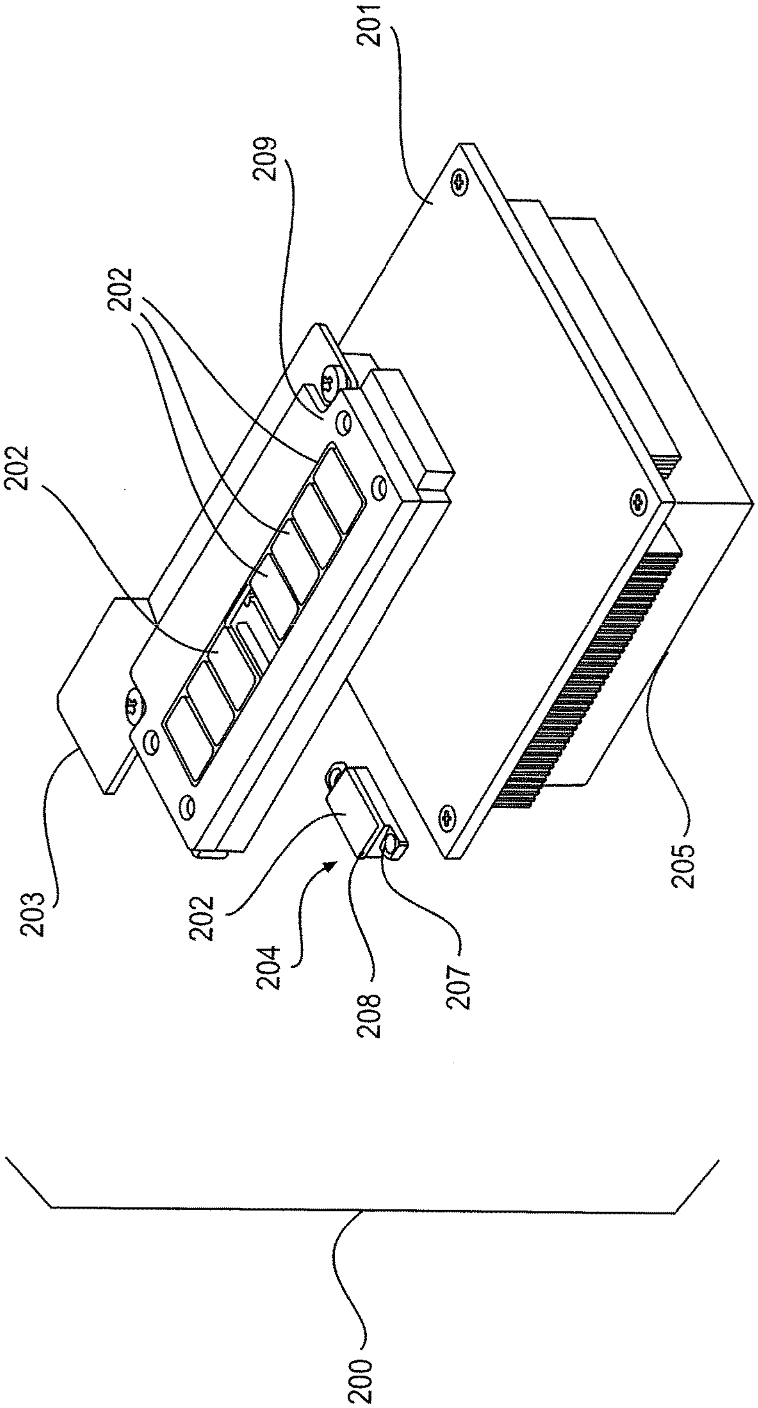
FIG. 1 is a diagram of an example of a heating and cooling module.

The following detailed description is presented to enable any person skilled in the art to make and use the invention. For purposes of explanation, specific nomenclature is set forth to provide a thorough understanding of the present application. However, it will be apparent to one skilled in the art that these specific details are not required to practice the invention. Description of specific embodiments and applications is provided only as representative examples. This description is an exemplification of the principles of the invention and is not intended to limit the invention to the particular embodiments illustrated.

This description is intended to be read in connection with the accompanying drawings, which are considered part of the entire written description of this invention. The drawing figures are not necessarily to scale and certain features of the invention may be shown exaggerated in scale or in somewhat schematic form in the interest of clarity and conciseness. In the description, relative terms such as "front," "back" "up," "down," "top" and "bottom," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

As used herein, the term "sample" includes biological samples such as cell samples, bacterial samples, virus samples, samples of other microorganisms, samples obtained from a mammalian subject, preferably a human subject, such as tissue samples, cell culture samples, stool samples, and biological fluid samples (e.g., blood, plasma, serum, saliva, urine, cerebral or spinal fluid, lymph liquid and nipple aspirate), environmental samples, such as air samples, water samples, dust samples and soil samples.

The term "nucleic acid," as used in the embodiments described hereinafter, refers to individual nucleic acids and polymeric chains of nucleic acids, including DNA and RNA, whether naturally occurring or artificially synthesized (including analogs thereof), or modifications thereof, especially those modifications known to occur in nature, having any length. Examples of nucleic acid lengths that are in accord with the present invention include, without limitation, lengths suitable for PCR products (e.g., about 50 to 700 base pairs (bp)) and human genomic DNA (e.g., on an order from about kilobase pairs (Kb) to gigabase pairs (Gb)). Thus, it will be appreciated that the term "nucleic acid" encompasses single nucleic acids as well as stretches of nucleotides, nucleosides, natural or artificial, and combinations thereof, in small fragments, e.g., expressed sequence tags or genetic fragments, as well as larger chains as exemplified by genomic material including individual genes and even whole chromosomes. The term "nucleic acid" also encompasses peptide nucleic acid (PNA) and locked nucleic acid (LNA) oligomers.

The term "hydrophilic surface" as used herein, refers to a surface that would form a contact angle of 45° or smaller with a drop of pure water resting on such a surface. The term "hydrophobic surface" as used herein, refers to a surface that would form a contact angle greater than 45° with a drop of pure water resting on such a surface. Contact angles can be measured using a contact angle goniometer.

One aspect of the present application relates to a molecular testing device. The device comprises a heating-and-cooling module and a combined amplification and hybridization reaction chamber. In some embodiments, the heating and cooling module comprises a heat transfer surface that is adapted to make contact with an exterior surface of the reaction chamber, and the reaction chamber comprises a microarray.

In some embodiments, the heating-and-cooling module comprises a plurality of TEHC devices and the same number of combined amplification and hybridization reaction chambers. The temperature in each reaction chamber is controlled by an individual TEHC device such that different heating/cooling programs may be applied to different reaction chambers. In some embodiments, the heating-and-cooling module comprises 2, 3, 4, 5, 6, 7, 8, 9, 10 or more TEHC devices and the same number of combined amplification and hybridization reaction chambers.

Heating and Cooling Module

In some embodiments, the heating and cooling module includes a thermoelectric heating and cooling (TEHC) device. One or more TEHC devices can be integrated into the module. In other embodiments, the heating and cooling module further comprises a temperature sensor. Examples of temperature sensors are resistance temperature detectors (RTDs), thermocouples, thermopiles, and thermistors. In some embodiments, the temperature sensors are RTDs. In other embodiments, the temperature sensors are thermistors, which have higher resolution, a smaller temperature range and larger drift over time. In some embodiments, a thermistor of the heating and cooling unit couples to an electronic analog-to-digital convertor (ADC).

In some embodiments, the TEHC device is a Peltier device. A Peltier device is a thermoelectric heating and cooling device that uses the Peltier effect to create a heat flux between the junction of two different types of materials. A Peltier device functions as a solid-state active heat pump that uses electrical energy to transfer heat from one side of the device to the other, depending on the direction of the current. Such an instrument can be used for either heating or cooling and is also called a Peltier heat pump, solid state refrigerator, or thermoelectric cooler (TEC). In some embodiments, the Peltier device is made of ceramic materials (e.g., Ferrotec Peltier cooler model 72001/127/085B). Examples of ceramic materials include: Alumina, Beryllium Oxide, and Aluminum Nitride.

In other embodiments, the TEHC device is a thin-film semiconductor (e.g., bismuth telluride). In other embodiments, the TEHC device is a thermoelectric couple made of p and n type semiconductors. Examples of p and n type semiconductors are bismuth antimony, bismuth telluride, lead telluride, and silicon germanium. This type of TEHC device has a response time that is shorter than the 1 to 3 second response time of ceramic TEHC devices. This characteristic allows rapid ramp rates and finer temperature control. In some embodiments, the TEHC device is a thin-film semiconductor having a response time less than 300 ms, 100 ms, 30 ms, 10 ms, 5 ms, 2 ms or 1 ms. In some embodiments, the TEHC devices have footprints (e.g., 2.4 mm×3.5 mm) that offer an ability to focus the heating and cooling towards a target area, such as the exterior surface of the reaction chambers of a flow cell. In some embodiments, the TEHC devices have footprints of 150 $mm^2$ or less, 50 $mm^2$ or less, 40 $mm^2$ or less, 30 $mm^2$ or less, 20 $mm^2$ or less, or 10 $mm^2$ or less. In other embodiments, the TEHC devices have footprints of about 8.7 mm×15 mm, 5 mm×10 mm, 4 mm×8 mm, 3 mm×6 mm or 2.4 mm×3.5 mm.

Furthermore, the high heat transfer power (e.g., Qmax/$cm^2$~80 $W/cm^2$ as compared to 3 $W/cm^2$ for ceramic Peltier devices) of these devices make them well suited for heating and cooling small flow cell reaction chambers. In some embodiments, the thin-film semiconductor thermoelectric devices are coupled to heat spreaders of larger geometries to interface with irregularly-shaped flow cell reaction chambers. These devices also offer resistance to vibration and are less susceptible to failure, caused by thermal cycling stress, than ceramic Peltiers.

FIG. 1 shows an embodiment of a heating and cooling module 200. In this embodiment, the heating and cooling module 200 includes a plurality of TEHC devices 204, each containing a heat spreader 208 with a heat transfer surface 202 and a heating and cooling unit 207; a platform (209, as shown, is a bezel to protect TEHC devices 204) holding the TEHC devices 204; and a heat sink 201 coupled to the other side of the TEHC devices 204. Examples of heat sinks 201 and heat spreader 208 are copper, aluminum, nickel, heat pipes, and/or vapor chambers. During operation, the heat transfer surface 202 makes intimate contact with an exterior surface of a reaction chamber of a flow cell (shown in FIGS. 2 and 3) and thus controls the temperature inside the reaction chamber of the flow cell. In some embodiments, the heating and cooling module 200 further comprises an integrated printed circuit board 203 and a fan 205 under the heat sink 201.

In some embodiments, the heat sink 201 and/or heat spreader 208 are coupled to the heating and cooling unit 207 of the TEHC device 204 with thermally conductive epoxy, thermally conductive adhesives, liquid metal (e.g., Gallium) or solder (e.g., Indium). In one embodiment the heat transfer surface 202 is flat. In some of these embodiments the heat spreader 208 has a heat transfer surface 202 in a rectangular shape with dimensions that range from 3 mm×3mm to 75 mm×80 mm, and preferably 8 mm×10 mm to 10 mm×20 mm. In some embodiments, the heat transfer surface 202 of the heat spreader 208 has an inlet section to heat a fluidic channel of the flow cell where the inlet section is smaller in size than the region that heats the reaction chamber. This inlet section can be rectangular and has the size range of 0.1 to 5 mm wide and 1 mm to 20 mm long. In another embodiment, the heat transfer surface 202 of the heat spreader 208 has an outlet section to heat a fluidic channel of the flow cell with a size range of 0.1 to 15 mm wide and 1 mm to 75 mm long. In some embodiments, the heat transfer surface 202 of the heat spreader 208 has three sections, an inlet heating section, a reaction chamber heating section, and an outlet heating section. The thickness of the heat spreader 208 is preferably 0.05 to 5 mm, and more preferably 0.1 to 1 mm, and even more preferably 0.15 to 0.6 mm.

Flow Cell

The term “flow cell,” as used herein, refers to a microarray-based detection device. In some embodiments, the flow cell comprises a reaction chamber having a sample inlet, a sample outlet and a microarray located therein. In some embodiments, the reaction chamber is a combined amplification and hybridization reaction chamber capable of performing both an amplification reaction, such as a PCR, and a hybridization reaction in the same chamber. In some embodiments, the flow cell further comprises a waste chamber that is in fluid communication with the reaction chamber. In some embodiments, the reaction chamber is coated with a hydrophilic material and has a hydrophilic surface positioned to facilitate complete filling of the reaction chamber and the fluid flow from the reaction chamber to the waste chamber. The hydrophilic surface contacts a liquid as it enters the reaction chamber from the sample inlet and allows complete filling of the microarray chamber. In certain embodiments, the reaction chamber is in the shape of an elongated channel of variable width and is directly connected to the waste chamber. In other embodiments, the microarray chamber is connected to the waste chamber through a waste channel.

In other embodiments, the flow cell comprises two or more reaction chambers, or an array of reaction chambers. In other embodiments, the flow cell comprises two or more reaction chambers or an array of reaction chambers and two or more waste chambers or an array of waste chambers, each reaction chamber is connected to a waste chamber through a waste channel. In still other embodiments, the flow cell comprises two or more reaction chambers or an array of reaction chambers and a single waste chamber, wherein each reaction chamber is connected to the waste chamber through a waste channel.

In some embodiments, the microarray is located on the bottom surface of the reaction chamber and the top surface, or at least a portion of the top surface, of the reaction chamber is coated with a hydrophilic material. Examples of the hydrophilic material include, but are not limited to, hydrophilic polymers such as polyethylene glycols, polyhydroxyethyl methacrylates, Bionite, poly(N-vinyl lactams), poly(vinylpyrrolidone), poly(ethylene oxide), poly(propylene oxide), polyacrylamides, cellulosics, methyl cellulose, polyanhydrides, polyacrylic acids, polyvinyl alcohols, polyvinyl ethers, alkylphenol ethoxylates, complex polyol mono-esters, polyoxyethylene esters of oleic acid, polyoxyethylene sorbitan esters of oleic acid, and sorbitan esters of fatty acids; inorganic hydrophilic materials such as inorganic oxide, gold, zeolite, and diamond-like carbon; and surfactants such as Triton X-100, Tween, Sodium dodecyl sulfate (SDS), ammonium lauryl sulfate, alkyl sulfate salts, sodium lauryl ether sulfate (SLES), alkyl benzene sulfonate, soaps, fatty acid salts, cetyl trimethylammonium bromide (CTAB) a.k.a. hexadecyl trimethyl ammonium bromide, alkyltrimethylammonium salts, cetylpyridinium chloride (CPC), polyethoxylated tallow amine (POEA), benzalkonium chloride (BAC), benzethonium chloride (BZT), dodecyl betaine, dodecyl dimethylamine oxide, cocamidopropyl betaine, coco ampho glycinate alkyl poly(ethylene oxide), copolymers of poly(ethylene oxide) and poly(propylene oxide) (commercially called Poloxamers or Poloxamines), alkyl polyglucosides, fatty alcohols, cocamide MEA, cocamide DEA, cocamide TEA.

In some embodiments, one or more surfactants are mixed with reaction polymers such as polyurethanes and epoxies to serve as a hydrophilic coating. In other embodiments, the top surface or the bottom surface of the reaction chamber is made hydrophilic by surface treatment such as atmospheric plasma treatment, corona treatment or gas corona treatment.

The microarray in the reaction chamber can be any type of microarray, including but not limited to oligonucleotide microarrays and protein microarrays. In one embodiment, the microarray is an antibody microarray and the microarray system is used for capturing and labeling target antigens. In one embodiment, the microarray is formed using the printing gel spots method described in e.g., U.S. Pat. Nos.5,741,700, 5,770,721, 5,981,734, 6,656,725 and U.S. patent application Ser. Nos. 10/068,474, 11/425,667 and 60/793,176, all of which are hereby incorporated by reference in their entirety. In certain embodiments, the microarray comprises a plurality of microarray spots printed on a microarray substrate that forms the bottom of the microarray chamber.

Figure 2:
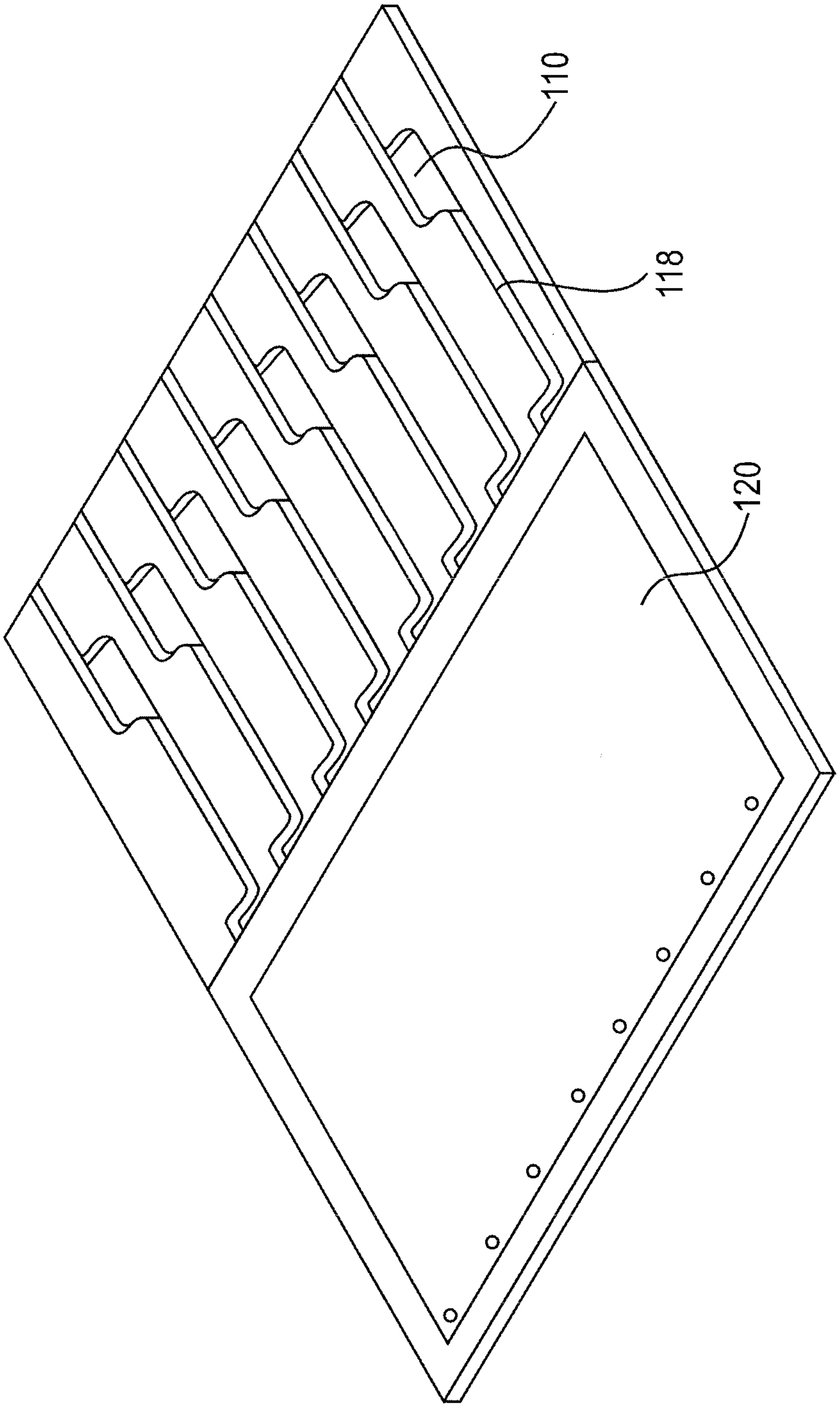
FIG. 2 is a diagram of an example of an array of flow cell reaction chambers and a waste chamber.

FIG. 2 shows an exemplary array of flow cell reaction chambers and a waste chamber. In this embodiment, the flow cell comprises multiple reaction chambers 110, each having a channel 118 that connects the sample outlet of the reaction chamber 110 to the inlet of the waste chamber 120. In one embodiment, the sidewall of channel 118 is hydrophobic to trap bubbles. In some embodiments, the cross-sectional area at the waste chamber end of the channel is at least 2-times, 3-times, 4-times or 5-times larger than the cross-sectional area at the reaction chamber end of the channel 118. In some embodiments, the channel 118 comprises a switchback section that contains two turns to form an S-shaped or Z-shaped channel section. In a further embodiment, the two turns are 90° turns.

Figure 3A:
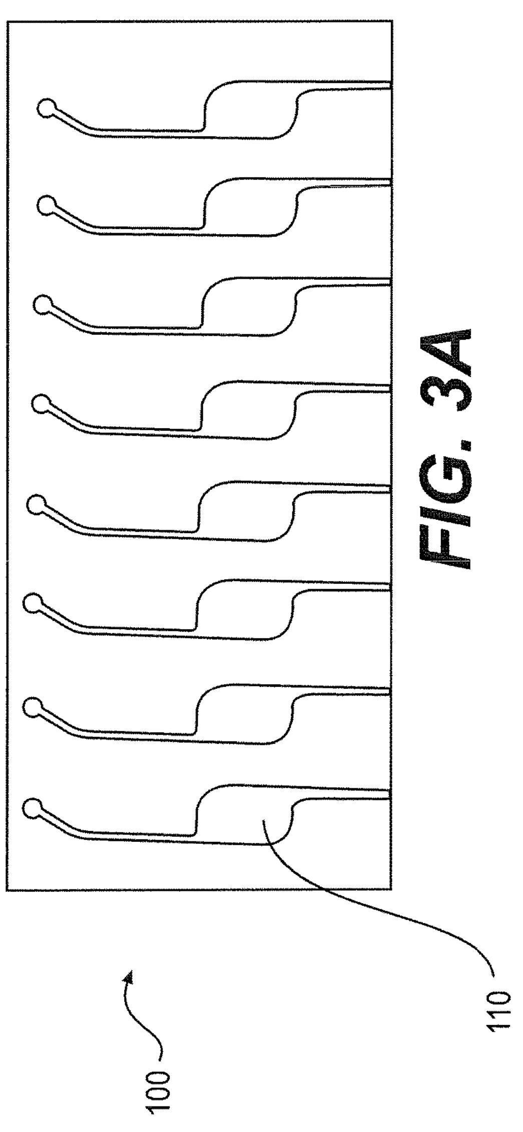
FIGS. 3A-3B are diagrams of an example of an array of flow cell reaction chambers.
Figure 3B:
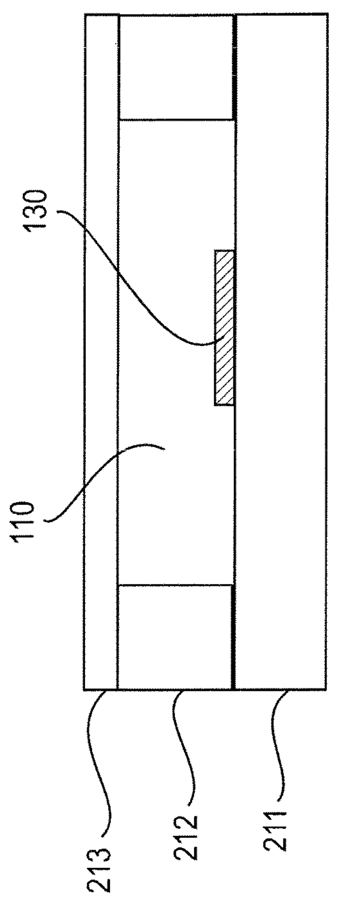

FIG. 3A shows another embodiment of a flow cell 100 with multiple reaction chambers 110. In this embodiment, the reaction chambers 110 are formed by a substrate 211, a spacer 212, and a cover 213 (FIG. 3B). Materials used to create the substrate 211, spacer 212, or the cover 213 include, but are not limited to, ceramics, plastics, elastomers and metals. Examples of ceramics include, but are not limited to, glass, silicon, silicon nitride, and silicon dioxide. Examples of plastics include polycarbonate, polyethylene (Low Density, High Density, UltraHigh Molecular Weight), polyoxymethylene, polypropylene, polyvinylidene chloride, polyester, polymethylmethacrylate, polyamide, polyvinylchloride, polystyrene, acrylonitrile butadiene styrene, and polyurethane. Examples of elastomers include, but are not limited to, natural polyisoprene, synthethic polyisoprene, polybutadiene, chloroprene, butyl rubber, styriene butadiene rubber, nitrile rubber, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoelectric elastomers, protein resilin, elastin, polysulfide rubber, and elastolefin. Examples of metals include, but are not limited to, aluminum, platinum, gold, nickel, copper, and alloys of these metals. These materials can be cast, extruded (e.g., films), machined, and/or molded into the proper shape.

In some embodiments, the substrate material is plastic with thermal conductivities of approximately 0.2 W/mK. In other cases the substrate material is glass with a thermal conductivity of about 1 W/mK. In some embodiments, the substrate material has a thermal conductivity in the range of 0.2 to 3 W/mK. In some embodiments, the substrate material has a thermal conductivity in the range of 3 to 30 W/mK. In some embodiments, the substrate material has a thermal conductivity in the range of 30 to 400 W/mK. In other embodiments, the substrate material has a thermal conductivity of at least 1, 3, 10, 30, 100 or 300 W/mK. In some embodiments, the spacer 212 is bonded to the cover 213 and the substrate 211. Bonding methods include adhesives, ultrasonic welding, laser welding, heat staking, solvent bonding, thermal bonding, and compression of an elastomeric spacer. Adhesives used for bonding can be in a liquid or viscoelastic form. Examples of adhesives include, but are not limited to, epoxies, acrylics, silicones, polysaccharides, and rubbers. Adhesive curing can be achieved with heat, pressure, ultraviolet irradiation, exposure to air, and or catalysts.

In another embodiment the spacer 212 and the substrate 211 are a single monolithic part. In yet another embodiment the spacer 212 and the cover 213 are a single monolithic part. In still yet another embodiment the substrate 211, spacer 212, and cover 213 are a single monolithic part.

In some embodiments, the reaction chamber 110 comprises one or more microarrays 130 formed on the substrate 211. In some embodiments, the one or more microarrays 130 are DNA microarrays, protein microarrays or mixtures thereof. As used herein, the term "microarray" refers to an ordered array of spots presented for binding to ligands of interest. A microarray consists of at least two spots. In some embodiments, the microarray consists of a single row of spots. In other embodiments, the microarray consists of a plurality of rows of spots. The ligands of interest include, but are not limited to, nucleic acids (e.g., molecular beacons, aptamers, locked nucleic acids, peptide nucleic acids), proteins, peptides, polysaccharides, antibodies, antigens, viruses, and bacteria.

Interface Between Heating and Cooling Module and Reaction Chamber

Figure 4:
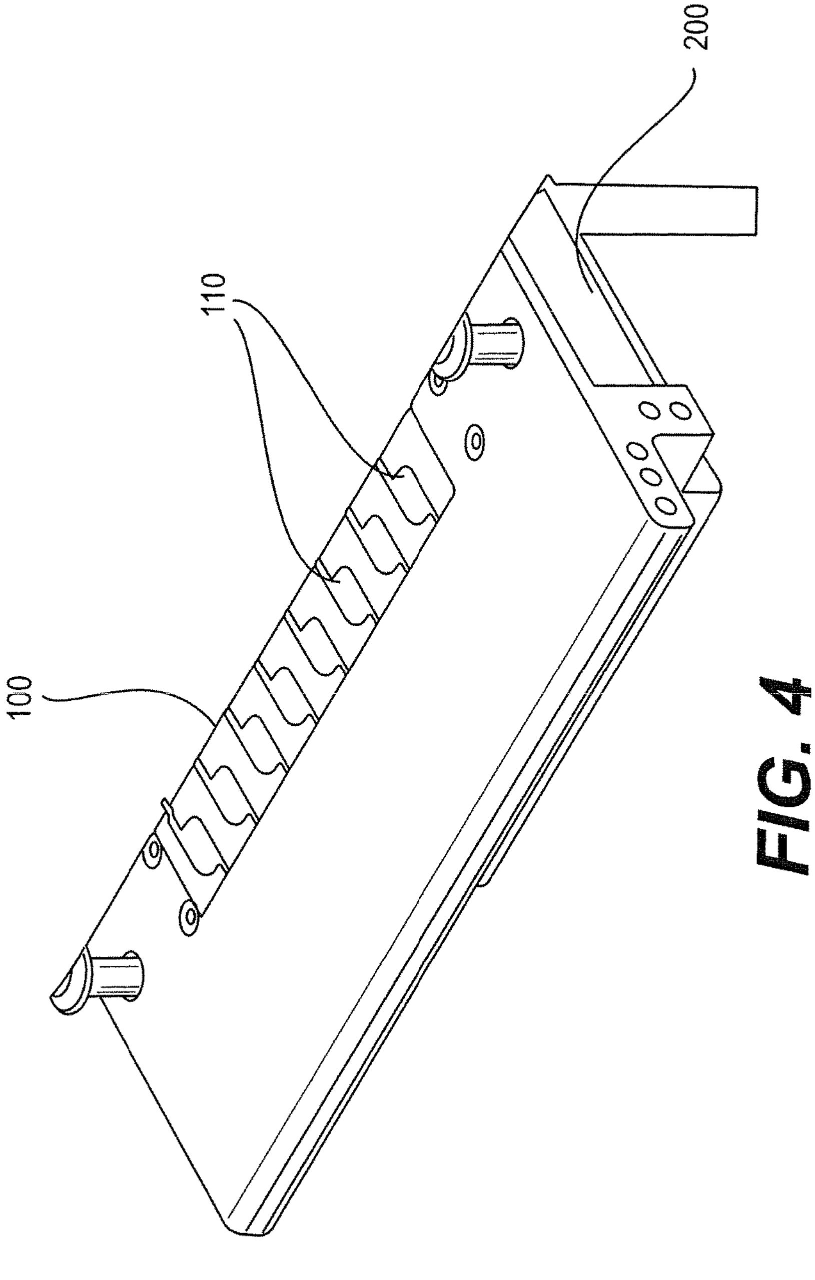
FIG. 4 is a diagram of an example of an array of flow cell chambers on top of heating and cooling modules.

In some embodiments, the flow cell 100 is placed on top of the heating and cooling module 200 so that the reaction chamber 110 is located on top of the heat transfer surface 202 of the heat and cooling devices. See FIG. 4. In some embodiments the heating and cooling module 200 is mounted to a moving system. In some embodiments the heat transfer surface of the heat and cooling devices absorbs light. Examples of how to achieve light absorption include painting the heat transfer surface 202 black, black anodizing, or coating it with black chrome by electroplating. Light absorption reduces scatter that can interfere with imaging microarrays. In some embodiments, thermal cycling occurs prior to imaging. In some embodiments thermal cycling occurs simultaneously with imaging.

Figure 5:
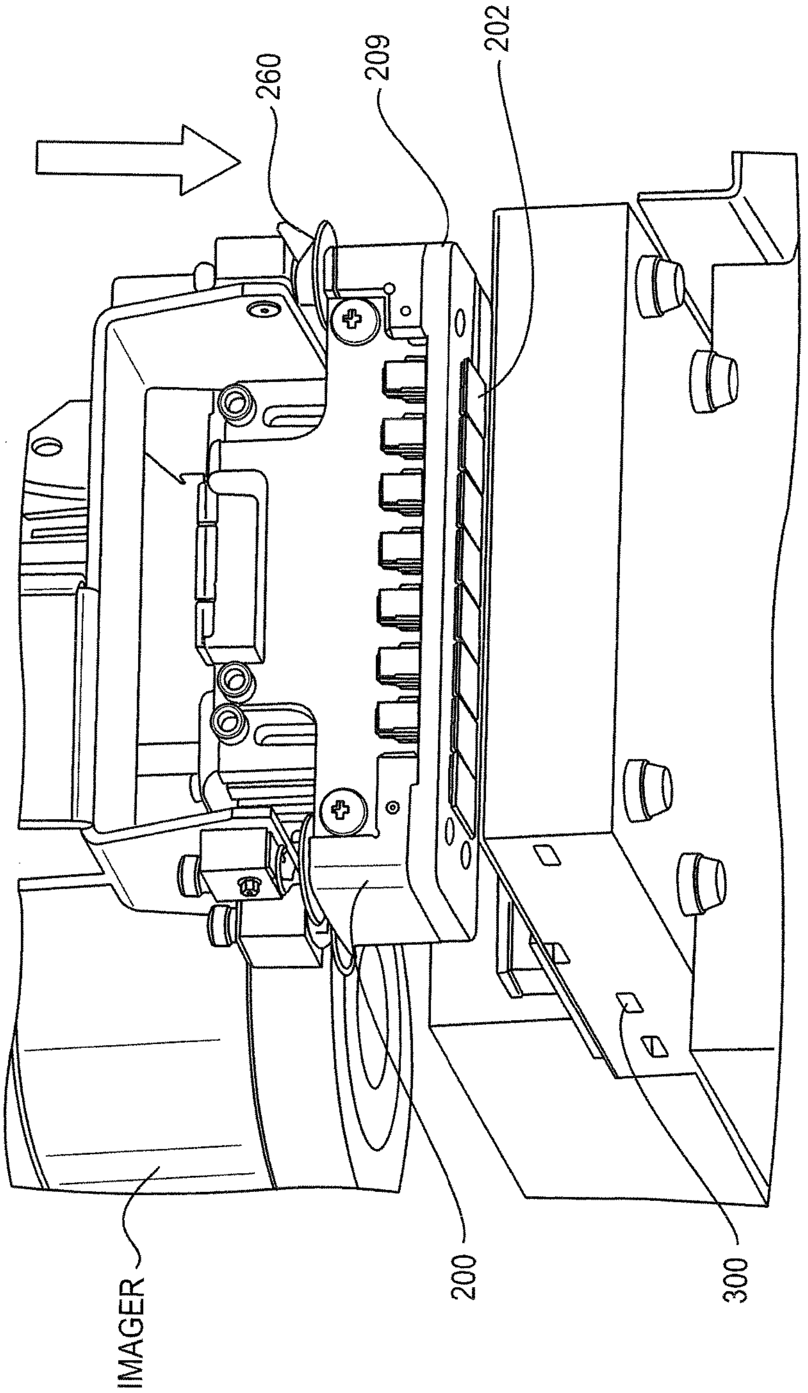
FIG. 5 is a diagram of an example of a heating and cooling module that is lowered on top of a flow cell.

In another embodiment the heating and cooling module 200 is adapted to descend down on the flow cell 100 sitting on flow cell holder 300, or flow cell holder 300 ascends up to the heating and cooling module 200, such that the reaction chambers 110 of the flow cell 100 make contact with the heat transfer surface 202 of the TEHC devices (see FIG. 5). In some embodiments, compressible devices are used to limit the force applied to the flow cell 100. In some embodiments, the compressible devices are located above the platform 209 on which the TEHC devices are mounted (See FIG. 5). In other embodiments, the compressible devices 260 are located below the flow cell 100 (see FIG. 6). In still other embodiments, the compressible devices are located both above the platform 209 and below the flow cell 100. Examples of compressible devices include, but are not limited to, springs, foam, memory foam, leaf springs, and deformable plastic or other materials such as silicon.

In some embodiments the external surfaces of the reaction chamber 110 that do not interface with the heat transfer surface 202 are insulated. In some embodiments the insulation is a component of the consumable. In other embodiments the insulation is a component of the instrument. In still other embodiments the insulation is a component on both the consumable and the instrument. Examples of insulation include dead air, Styrofoam, polyurethane foam, Aerogel, fiberglass, and plastic. In some embodiments, the insulation layer 270 absorbs light. The effect of insulation can be modeled as follows:

$$T_{offset} = T_{TEC} - T_{liquid} \propto \frac{1}{R_{insulation}}(T_{TEC} - T_{ambient})$$

where $T_{offset}$ is the difference between the set temperature and the actual temperature, $T_{TEC}$ is the temperature of the heat spreader, $T_{liquid}$ is the temperature of the liquid, and $R_{insulation}$ is the thermal resistance of the insulation layer.

Figure 6:
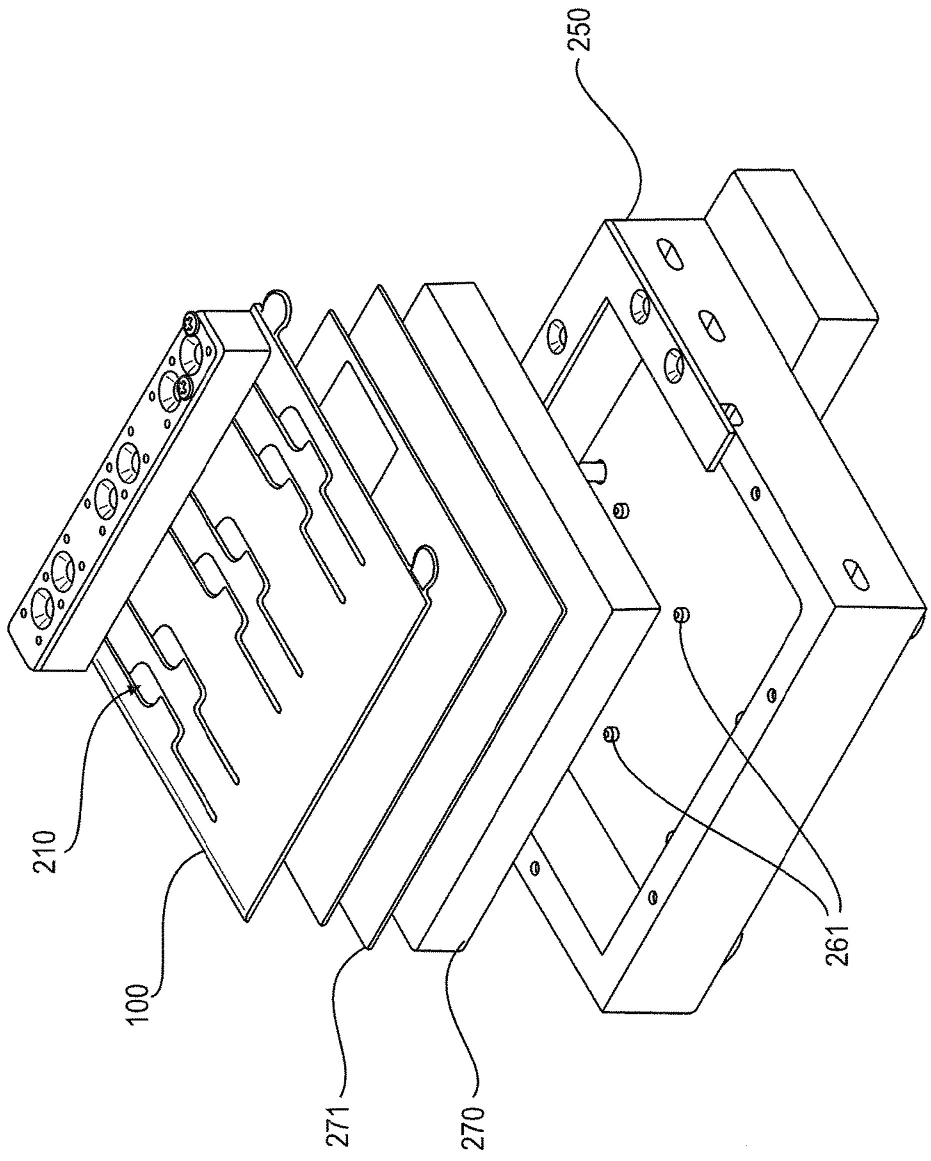
FIG. 6 is a diagram of a flow cell on top of a light absorbing layer, an insulation layer and a supporting base.

FIG. 6 shows an embodiment wherein the flow cell 100 is insulated on one side with the insulation layer 270. In this embodiment, a light absorbing material 271, such as black foil, separates the insulation layer 270 from the flow cell 100. The compressible devices are mounted below the insulation layer 270. The base 250 comprises locating features 261 for the compressible device. In some embodiments, the locating feature 261 is a stud, pin or peg. In other embodiments, the locating feature 261 is a cavity, hole or depression. In still other embodiments, the locating feature 261 is a cavity, hole or depression with a stud, pin or peg in its center.

In other embodiments, a single reaction chamber 110 may interface with two or more TEHC devices 204. In one embodiment, one TEHC device 204 interfaces with the top surface of the reaction chamber 110, while another TEHC device 204 interfaces with the bottom surface of the reaction chamber 110.

In another related embodiment, the heating-and-cooling modules 200 comprises a plurality of TEHC devices 204 that interface with an equal number of reaction chambers 110 in a flow cell 100, wherein each TEHC device 204 comprises a heat transfer surface 202 that is adapted to make contact with an exterior surface of a corresponding reaction chamber 110. In some embodiments, the TEHC devices 204 are attached to a common heat sink 201. In some embodiments, all the TEHC devices 204 are controlled by a single controller. In other embodiments, each TEHC device 204 is separately controlled so that a different reaction may be performed in each reaction chamber 110.

Figure 7:
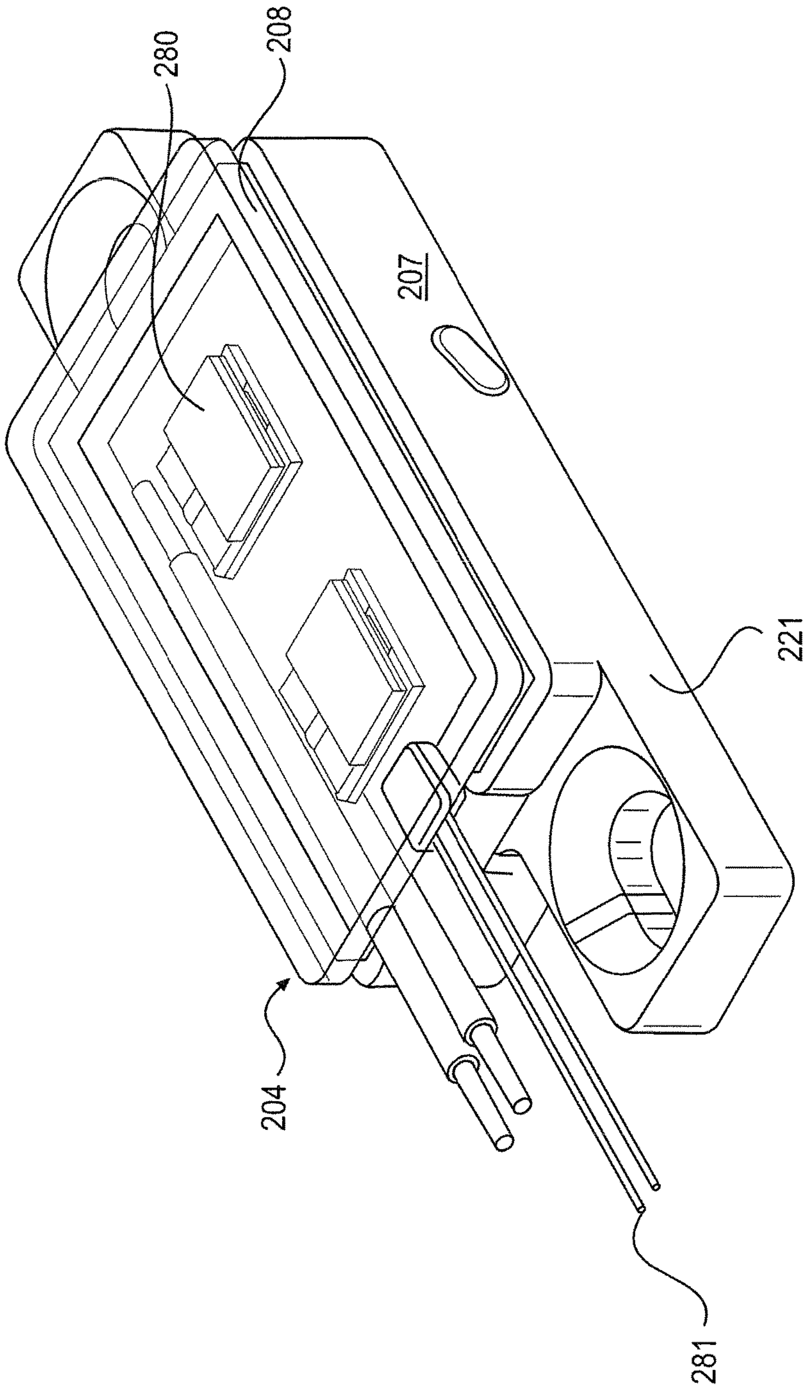
FIG. 7 is a diagram showing a thermoelectric heating and cooling (TEHC) device with two thin-film thermoelectric heating and cooling chips within the heat and cooling unit.
Figure 8A:
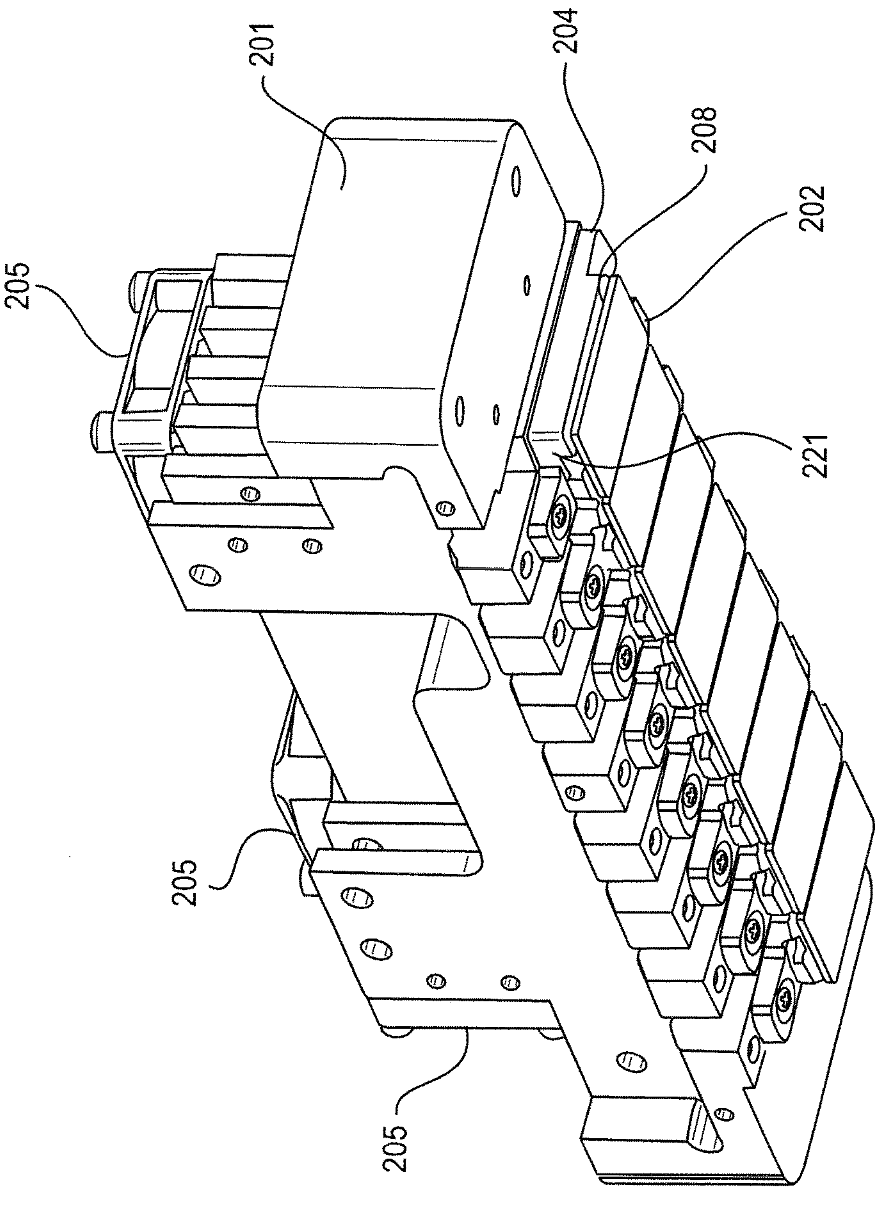
FIGS. 8A-8F are diagrams showing different views of a heating and cooling module with multiple TEHC devices.
Figure 8B:
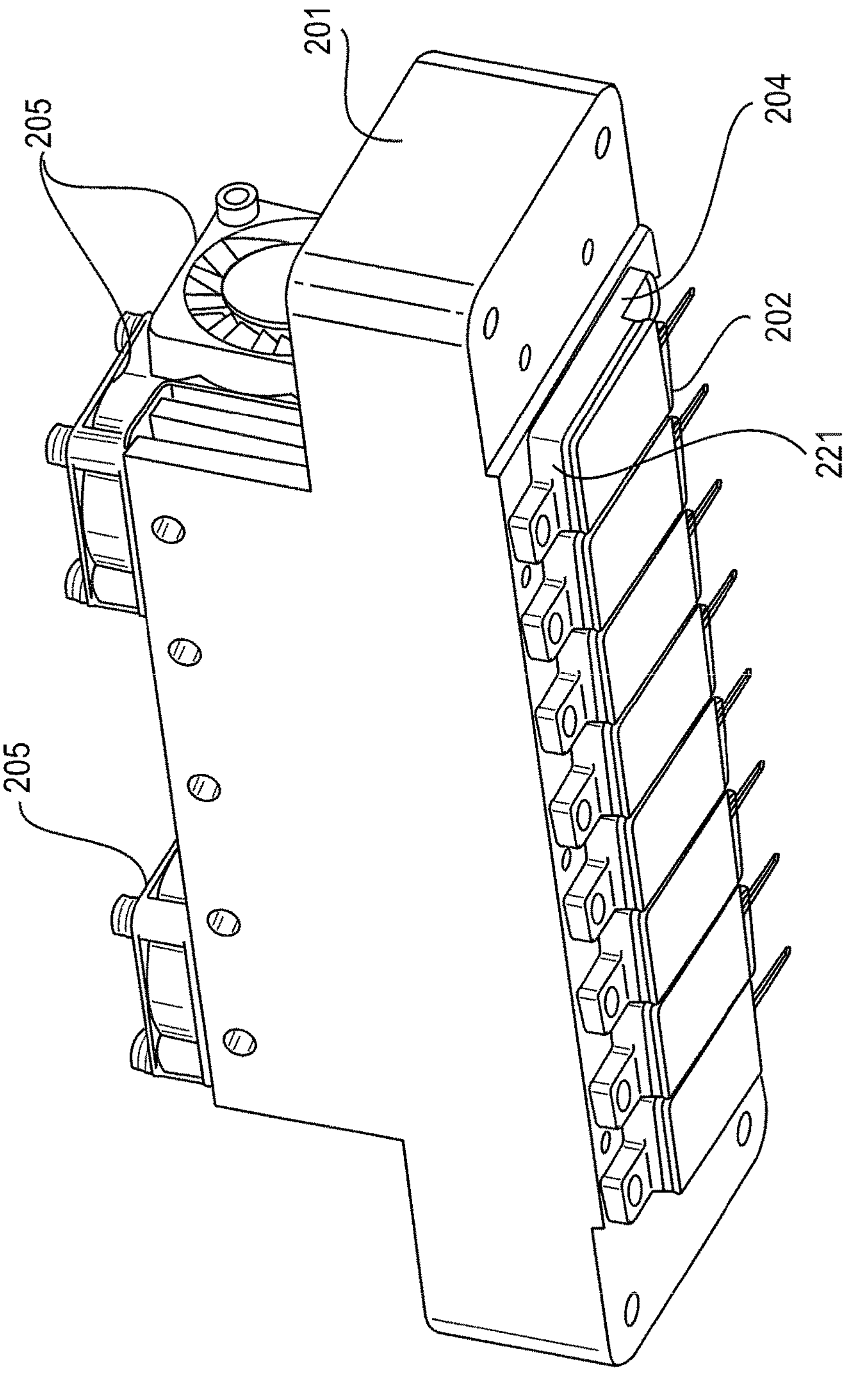
Figure 8C:
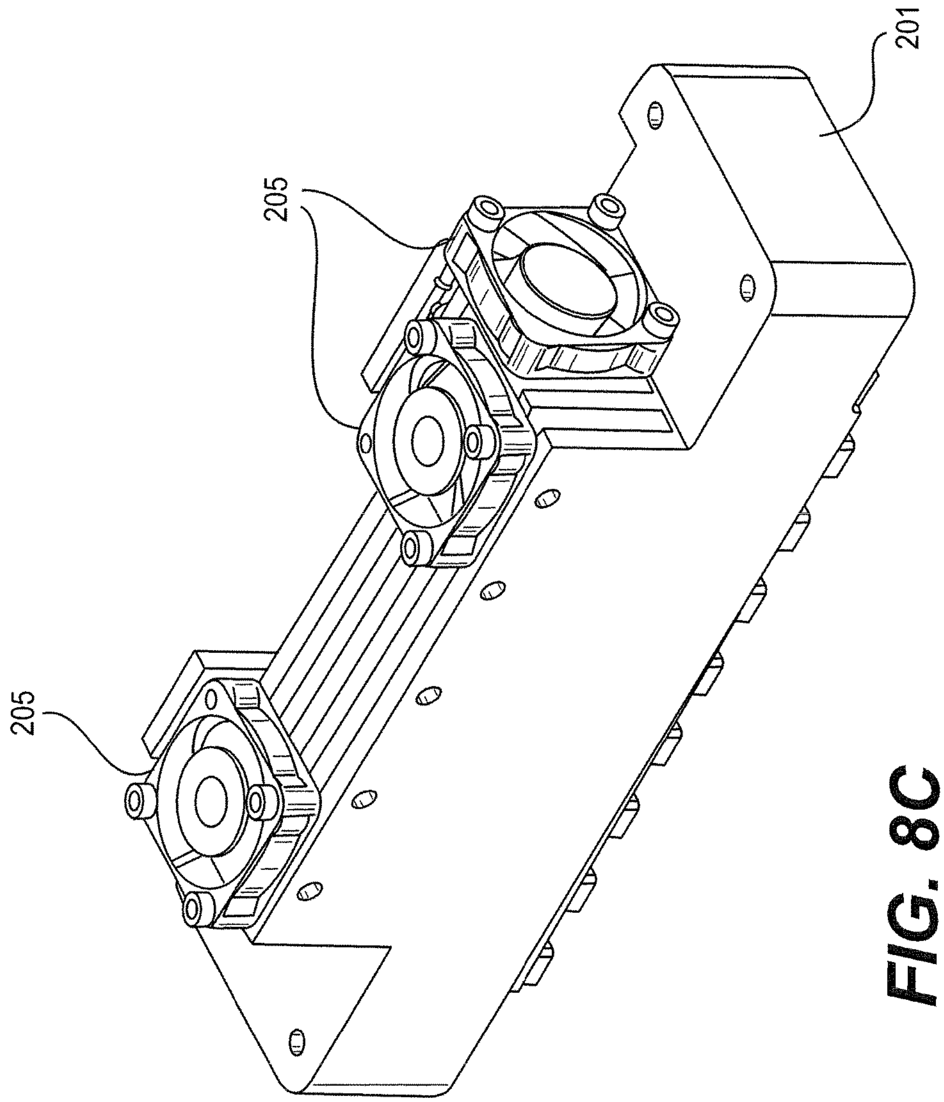
Figure 8D:
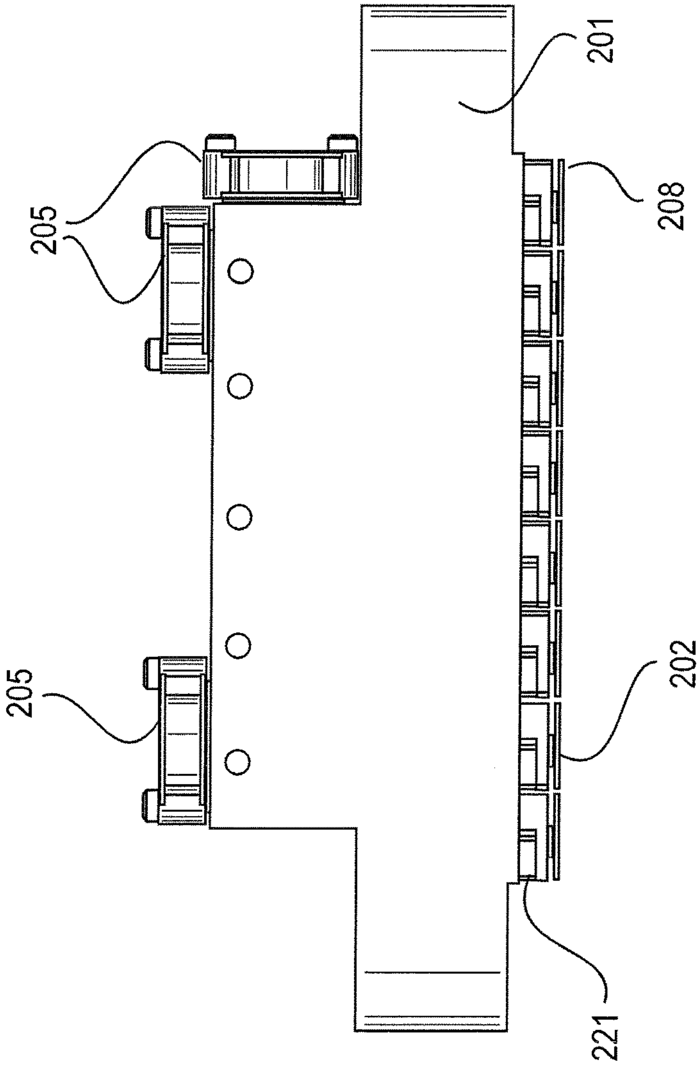
Figure 8E:
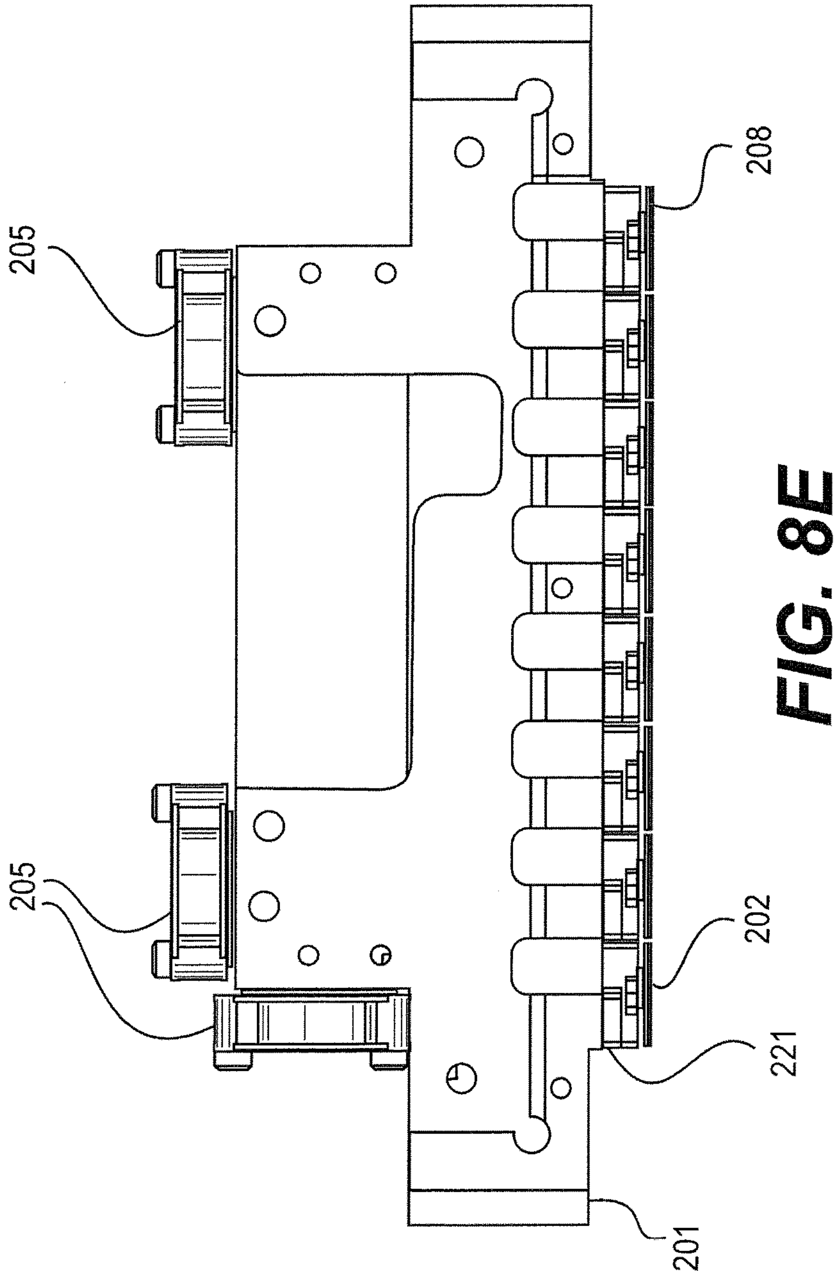
Figure 8F:
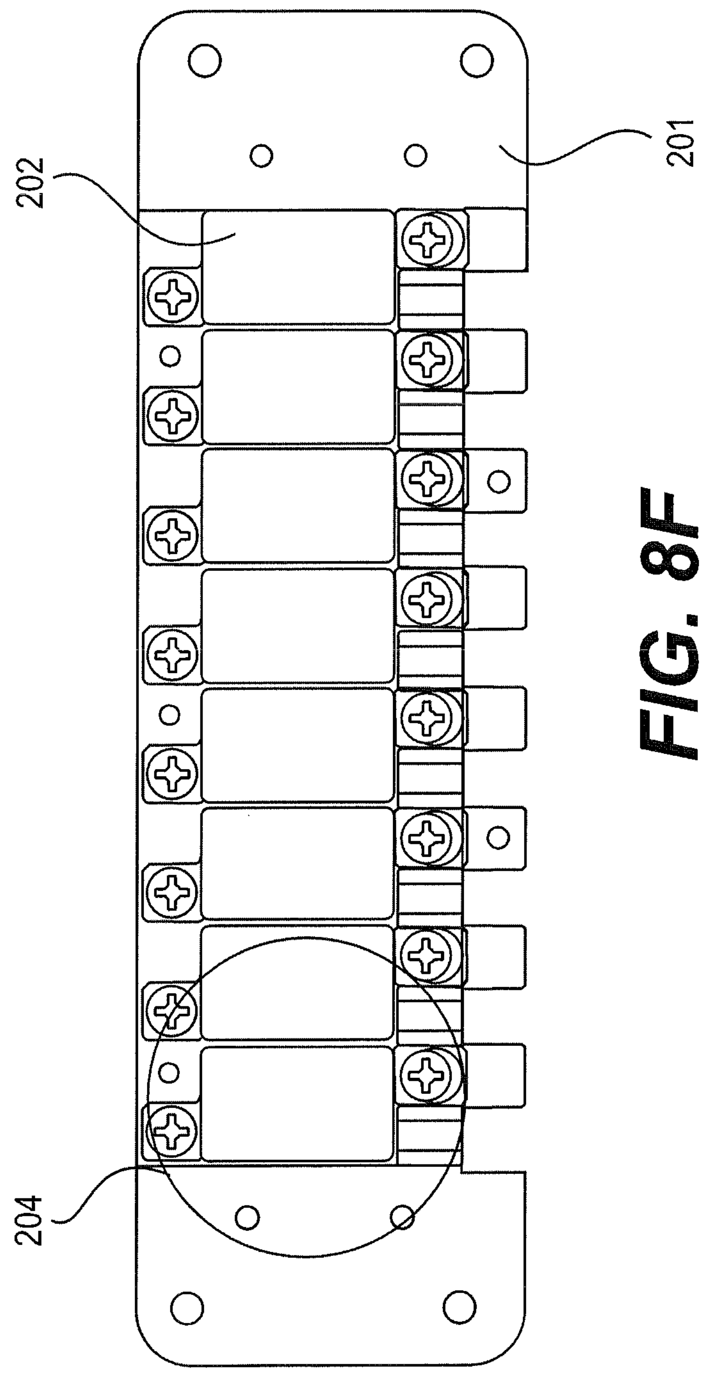

FIG. 7 shows an embodiment of a TEHC device 204 with two thin-film thermoelectric chips 280 mounted within the heating and cooling unit 207. The thin-film thermoelectric chips 280 are manufactured with aluminum nitride semiconductors and are mounted to a primary heat sink 221 with Indium solder and to a heat spreader 208 with Gallium liquid metal. The heat spreader 208 is 0.6 mm thick copper with a nickel coating. A polyimide sheet spacer serves as a standoff between the heat sink and the heat spreader 202. A thin-film RTD 281 is attached to the heat spreader 208 as well.

FIGS. 8A-8F show different views of another exemplary heating and cooling module 200 with multiple TEHC devices 204. Each TEHC device 204 comprises a heat spreader 208 with a heat transfer surface 202 and a heating/cooling unit with the primary heat sink 221. The multiple TEHC devices 204 are attached with a common, secondary heat sink 201 with multiple fans 205.

Control Scheme for Thermal Cycling

In some embodiments the heating-and-cooling module is controlled such that the set point temperature changes during the ramping state as a means of accelerating the approach to the desired temperature. In some embodiments the set point is artificially set within a range of −5° C. to 5° C. above the desired temperature The heating-and-cooling module 250 performs thermal cycling protocols that might include cycling between two temperatures, cycling across three temperatures, a prolonged hold temperature for storage or hybridization, and Touch Down PCR protocol. Temperature transitions may follow a step change, a sawtooth waveform, or sinusoidal waveform. These waveforms can also occur about a specific set temperature to induce thermally-convective mixing.

An aspect of the present application relates to a molecular testing device, comprising: a heating and cooling module comprising a thin-film thermoelectric heating and cooling device; and a removable test module comprising a combined amplification and hybridization reaction chamber comprising a thermo-conductive exterior surface and a microarray on an interior surface; wherein said thermoelectric heating and cooling device comprises a heat transfer surface that is adapted to make contact with said thermo-conductive exterior surface of said reaction chamber.

In some embodiments, the thin-film thermoelectric heating and cooling device is a Peltier device. In some further embodiments, the Peltier device is a ceramic Peltier device.

In other embodiments, the thin-film thermoelectric heating and cooling device comprises a thin-film semiconductor comprising bismuth antimony, bismuth telluride, lead telluride or silicon germanium. In some further embodiments, the thin-film semiconductor comprises bismuth telluride.

In still other embodiments, the thin-film thermoelectric heating and cooling device is a thermoelectric couple made of p and n type semiconductors. In some further embodiments, the the p and n type semiconductors are selected from the group consisting of bismuth antimony, bismuth telluride, lead telluride, and silicon germanium.

In yet other embodiments, the microarray is a gel spot microarray.

In some embodiments, the reaction chamber further comprises an exterior surface that is insulated with a thermal insulation material.

In other embodiments, the removable test module further comprises a waste chamber.

In still other embodiments, the removable test module comprises a plurality of combined amplification and hybridization reaction chambers, wherein each chamber comprises a thermo-conductive exterior surface, and wherein said heating and cooling module comprises a plurality of thermoelectric heating and cooling device, wherein each of said plurality of thermoelectric heating and cooling device comprises a heat transfer surface adapted to make contact with a thermo-conductive exterior surface of an amplification and hybridization reaction chamber.

In yet other embodiments, the heating and cooling module further comprises a temperature sensor. In some further embodiments, the temperature sensor comprises a thermistor or resistance thermal device.

Another aspect of the present application relates to a device for performing a polymerase chain reaction (PCR), comprising: a heating and cooling module comprising a thin-film thermoelectric heating and cooling device comprising a heat transfer surface; a holder for receiving a removable test module comprising a reaction chamber having a thermo-conductive exterior surface; a moving system that brings said heat transfer surface in contact with said thermo-conductive exterior surface when said test module is placed in said holder; and a programmable control module that regulates temperature of said heat transfer surface.

In some embodiments, the thermoelectric device is a Peltier device. In some further embodiments, the thermoelectric heating and cooling device comprises a thin-film semiconductor and a heat sink.

In other embodiments, the heating and cooling module further comprises a temperature sensor. In some further embodiments, the temperature sensor comprises a thermistor or resistance thermal device.

In still other embodiments, the heating and cooling module comprises a plurality of thin-film thermoelectric heating and cooling devices each comprising a heat transfer surface, wherein said removable test module comprises a plurality of reaction chambers each having a thermo-conductive exterior surface, wherein said programmable control module is capable of regulating temperature of each of said heat transfer surface individually in order to perform PCR under different conditions in each reaction chamber.

Yet another aspect of the present application relates to a method for performing a polymerase chain reaction (PCR) on a microarray in a reaction chamber. The method comprises several steps, including placing a test module comprising a reaction chamber into a PCR device, wherein said reaction chamber comprises a thermo-conductive exterior surface and a microarray mounted on an interior surface, and wherein said PCR device comprises a heating and cooling module comprising a thin-film thermoelectric heating and cooling device with a heat transfer surface, and a programmable control module that regulates temperature of said heat transfer surface. The method further comprises the step of bringing said heat transfer surface of said thin-film thermoelectric heating and cooling device into contact with said thermo-conductive exterior surface of said reaction chamber. The method also comprises the step of completing a PCR by heating and cooling said reaction chamber through said heat transfer surface based on a PCR program stored in said control module.

The present invention is further illustrated by the following examples which should not be construed as limiting. The contents of all references, patents and published patent applications cited throughout this application, as well as the Figures and Tables are incorporated herein by reference.

EXAMPLES

Example 1

Demonstration of the Effects of Insulation

Figure 9:
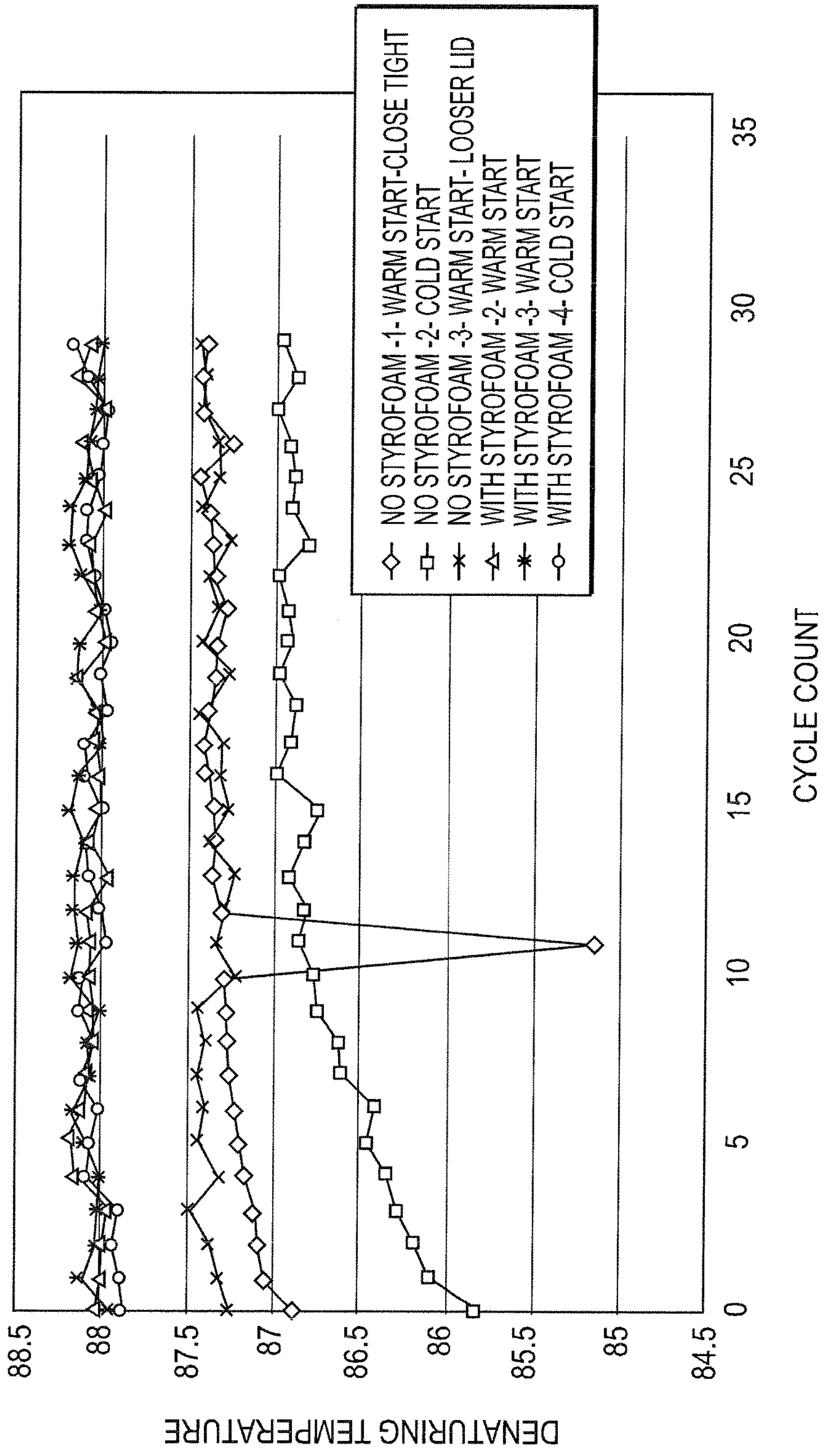
FIG. 9 shows that insulating the exposed portions of the reaction chamber reduces the temperature offset between the set temperature and the actual temperature measured by a resistance temperature detector (RTD) at the center of the reaction chamber.

A thin-film RTD (Minco RTD Model S39) is incorporated into a reaction chamber (0.5 mm thick), filled with thermal paste, and placed on a flat block Quanta thermocycler. One reaction chamber includes a one inch thick Styrofoam insulation layer and the other does not have insulation. The two reaction chambers are sequentially introduced onto the thermocycler. The thermal cycling protocol is 30 cycles of 88° C. for 60 seconds followed by 55° C. for 60 seconds. Only the denaturing temperatures are plotted. Temperature measurements represent a moving average of 20 seconds. As can be seen from FIG. 9, there can be a temperature offset of 1° C. from the 88° C. set point when the reaction chamber is not insulated.

Example 2

Demonstration of PCR when Using Heating and Cooling Module and Reaction Chamber The reaction chamber is comprised of a Questar™ substrate, an 0.5 mm double-sided pressure sensitive adhesive spacer tape, and a cover film. The reaction chamber volume is filled with approximately 50 μL. The reaction chamber has an inlet and an outlet hole.

The reaction chamber is filled 1×Qiagen QuantiFast RT-PCR mix (Qiagen, Valencia, Calif., US) containing primer mix, 10 ng of human genomic DNA from NIST SRM 2372 kit, and $10^4$ copies of purified *Streptococcus pyogenes* and influenza A nucleic acid.

Primers are asymmetric in concentration, and the higher concentration of primer is labeled with a fluorophore. Following PCR, the fluorescently-labeled amplicon hybridizes to probes in the gel spots on the microarray surface.

The thermal cycling protocol was 12.5 min at 47° C.; 5 min at 88° C.; and 35 cycles of 88° C. for 30 s and 52.5° C. for 35 s.

A control experiment was performed using amplification in a PCR tube on a conventional MJ thermocycler using the same mastermix as above and the following thermal cycling protocol was 12.5 min at 47° C.; 5 min at 88° C.; 35 cycles at 88° C. for 15 s and 52.5° C. for 20 s.

Following PCR, the mastermix was removed from the chamber and hybridized for 1 hr at 50° C. to a microarray printed on a glass substrate.

FIG. 10 shows fluorescent signal intensities from the microarray spots for the *S. pyogenes* and influenza A probes. The data show comparable results between the heating and cooling device with reaction chamber and the conventional thermal cycler with PCR tube.

Example 3

Demonstration of PCR when Heating and Cooling Module is Lowered onto Reaction Chamber A heating and cooling module 200 as described in Example 2 is mounted to a mechanical device that has a linear actuator that is used to lower the assembly onto the reaction chamber (see FIG. 5). The assembly consists of 4 springs that compress when lowered onto the reaction chamber.

Six reaction chambers similar to that of Example 2 are constructed and attached to PVC Foam Insulation foam with double sided tape.

The reaction chambers are filled with PCR mastermix and 33 pg of purified *Mycobacterium tuberculosis* (MTB) DNA from ATCC.

The following thermal cycling protocol is 88° C. for 7.5 min, and 50 cycles of 88° C. for 30 seconds and 55° C. for 60 seconds.

The product from the PCR mastermix is mixed with a hybridization buffer and incubated on a gel drop microarray, which includes probes for katG (a gene with possible mutations that confer drug resistance to isoniazid) and MTB. This is added to 25-μL Frame seal chambers (Biorad) with a Parafilm cover and incubated for 3 h at 55° C. Following incubation, the slides are agitated for 5 min in a bath consisting of 1× SSPE buffer with 0.01% Triton X-100. The slides are then dried by centrifugation at 2,300 rpm for 2 min.

Imaging is accomplished on an Akonni imaging system (see U.S. Pat.No. 8,623,789; herein incorporated by reference in its entirety) for 0.2 seconds and analyzed with Akonni software.

Figure 11:
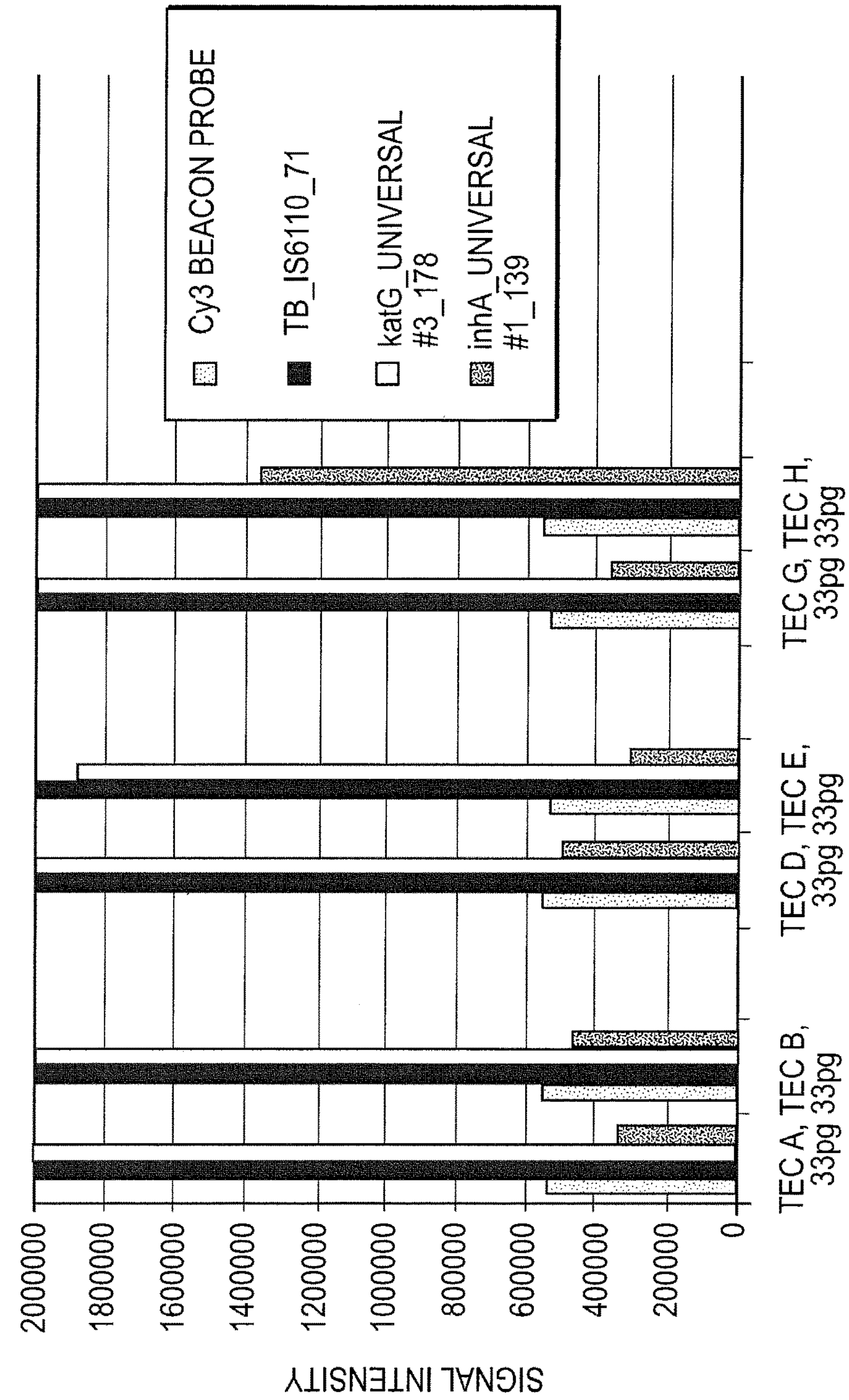
FIG. 11 shows results when performing PCR with the heating and cooling module lowered on top of the reaction chamber.

Signal intensities from the software are shown in FIG. 11. The data in FIG. 11 shows positive amplification and detection from the microarray spots that have probes for MTB and katG when challenged with wild-type MTB DNA.

Example 4

Combined PCR and Hybridization in Reaction Chamber

N-acetyl cysteine, sodium hydroxide digested sputum was amended with $10^7$ cfu/mL of H37Ra cells. Homogenization and lysis was accomplished using the device described in U.S. Pat. No. 8,399,190 (herein incorporated by reference in its entirety). Extraction of DNA was accomplished using the device and method described in U.S. Pat. Nos. 8,236,553 and 8,574,923 (herein incorporated by reference in their entirety).

Purified MTB DNA was mixed with PCR reagents described in Example 3 and added to a reaction chamber, similar to that of Example 2. The combined PCR and hybridization protocol was as follows: 7.5 min at 90.5° C., followed by 50 cycles of 90.5° C. for 30 seconds and 56° C. for 60 seconds, and 3 hr of hybridization at 55° C.

Figure 12:
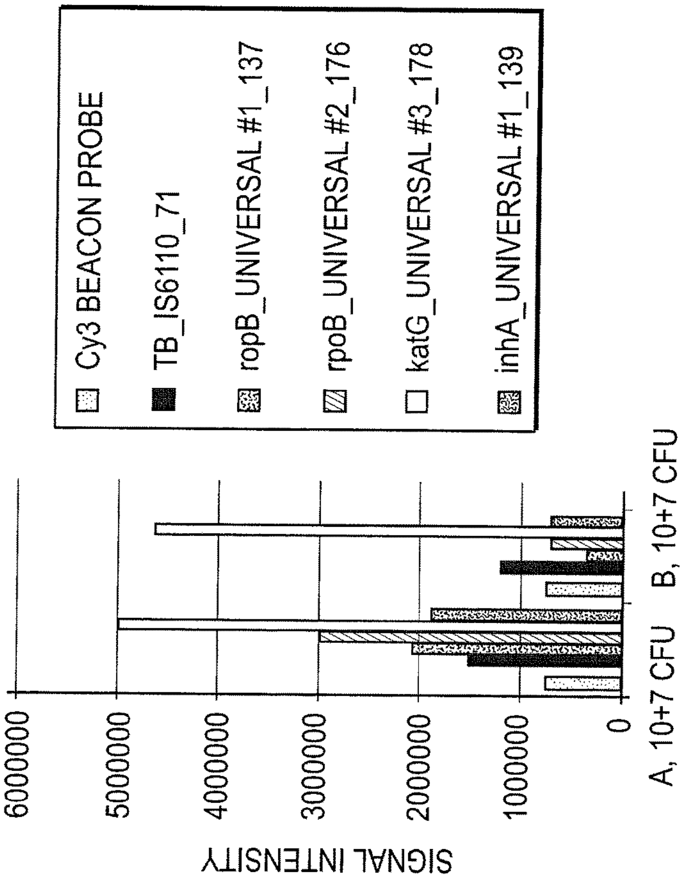
FIG. 12 shows combined PCR and hybridization in the reaction chamber when the heating and cooling module is lowered on top of the reaction chamber.

Following this protocol, the reaction chamber is washed with 300 μL of 1×SSPE and imaged for 0.2 seconds using a similar optical train as described in U.S. Pat. No. 8,623,789. The image is analyzed and signal intensities from gel drops are extracted and plotted in FIG. 12. FIG. 12 shows successful amplification and detection of markers for MTB, katG, inhA (a gene with possible mutations that confer drug resistance to isoniazid; this isolate is wildtype), and rpoB (a gene with possible mutations that confer drug resistance to rifampin; this isolate is wildtype).

The above description is for the purpose of teaching the person of ordinary skill in the art how to practice the present invention, and it is not intended to detail all those obvious modifications and variations of which will become apparent to the skilled worker upon reading the description. It is intended, however, that all such obvious modifications and variations be included within the scope of the present invention.

What is claimed is:

1. A device for performing a polymerase chain reaction (PCR), comprising:

a heating and cooling module comprising a thermoelectric heating and cooling device comprising a heat transfer surface;

a holder for receiving a removable test module comprising a reaction chamber having a therm-conductive exterior surface, an exterior bottom surface and a microarray on an interior surface, wherein the microarray is an ordered array of spots presented for binding to ligands of interest, wherein said thermoelectric heating and cooling device heats and cools depending on the direction of an electrical current said reaction chamber by contacting said heat transfer surface with said thereto-conductive top exterior surface of said reaction chamber, and wherein said holder comprises a thermal insulation layer to insulate said exterior bottom surface of said reaction chamber;

a moving system that brings said heat transfer surface in contact with said thermo-conductive exterior surface when said test module is placed in said holder, wherein said heat transfer surface undergoes thermal cycling during said PCR; and a programmable control module configured to control the direction of an electrical current flowing through said thermoelectric heating and cooling device to control the heating and cooling of said thermoelectric heating and cooling device.

2. The device of claim 1, wherein said thermoelectric device is a Peltier device.

3. The device of claim 1, wherein said thermoelectric heating and cooling device comprises a semiconductor and a heat sink.

4. The device of claim 1, wherein said heating and cooling module further comprises a temperature sensor.

5. The device of claim 4, wherein said temperature sensor comprises a thermistor or resistance thermal device.

6. The device of claim 1, wherein said heating and cooling module comprises a plurality of thermoelectric heating and cooling devices each comprising a heat transfer surface, wherein said removable test module comprises a plurality of reaction chambers each having a thermo-conductive exterior surface, wherein said programmable control module is capable of regulating temperature of each of said heat transfer surface individually in order to perform PCR under different conditions in each reaction chamber.

* * * * *